(12) United States Patent
Such et al.

(10) Patent No.: US 8,211,989 B2
(45) Date of Patent: Jul. 3, 2012

(54) CROSSLINKING METHOD

(75) Inventors: Christopher Henry Such, Mount Eliza (AU); Jim Patel, Parkdale (AU); William Roy Jackson, Camberwell (AU); Andrea Jane Robinson, St Kilda (AU); Algirdas Kazimleras Serelis, Mount Waverley (AU)

(73) Assignees: Monash University, Victoria (AU); Duluxgroup (Austrailia) Pty. Ltd, Victoria (AU)

( * ) Notice: Subject to any disclaimer, the term of this patent is extended or adjusted under 35 U.S.C. 154(b) by 260 days.

(21) Appl. No.: 11/988,180

(22) PCT Filed: Jun. 30, 2006

(86) PCT No.: PCT/AU2006/000930
§ 371 (c)(1),
(2), (4) Date: Mar. 5, 2009

(87) PCT Pub. No.: WO2007/002999
PCT Pub. Date: Jan. 11, 2007

(65) Prior Publication Data
US 2009/0186976 A1 Jul. 23, 2009

(51) Int. Cl.
*C09D 11/10* (2006.01)
*C08F 2/00* (2006.01)
*C07C 49/04* (2006.01)
*C07C 27/10* (2006.01)

(52) U.S. Cl. ..... 526/238.3; 526/75; 568/417; 562/512.2

(58) Field of Classification Search .................. 524/547, 524/570; 526/321, 238.3, 75, 317.1, 348; 526/280, 281, 335; 568/417, 459; 562/512.2; 428/420; 427/508; 260/42.44, 42.53, 42.21, 260/42.32, 878; 585/643
See application file for complete search history.

(56) References Cited

U.S. PATENT DOCUMENTS

| 4,049,616 A | 9/1977 | Scott et al. |
| 4,545,941 A * | 10/1985 | Rosenburg ................. 554/163 |
| 6,800,170 B2 | 10/2004 | Kendall et al. |
| 2002/0053379 A1 | 5/2002 | Tokas et al. |
| 2005/0070750 A1 * | 3/2005 | Newman et al. .............. 585/643 |
| 2005/0154221 A1 * | 7/2005 | Lysenko et al. ............... 554/174 |

FOREIGN PATENT DOCUMENTS

| WO | WO 96/19287 A1 | 6/1996 |
| WO | WO 02/076920 A1 | 10/2002 |
| WO | WO 2004/037754 A2 | 5/2004 |

OTHER PUBLICATIONS

Refvik, Ruthenium-Catalyzed Metathesis of Vegetable Oils, JAOCS, vol. 76,No. 1 (1999) 93-98.*
J.C. Mol, Application of olefin metatesis in oleochemistry: an example of green chemistry, 2002, Green Chemistry, 4, 5-13.*
Erhan, et al., "Drying Properties of Metathesized Soybean Oil," J. Am. Oil Chem. Soc., 1997, v74, n6, pp. 703-706.
Refvik, et al., "Ruthenium-Catalyzed Metathesis of Vegetable Oils," J. Am. Oil Chem. Soc. 1999, v76, n1, pp. 93-98.
Mol, J.C., "Application of olefin metathesis in oleochemistry: an example of green chemistry." Green Chemistry, 2002, v4, pp. 5-13.
Joly, et al., "Crosslinking of Cellulose by Olefin Metathesis," J. Carbohydr. Chem. 2003, v22, n1, pp. 47-55.
Boelhouwer, et al., "Metathesis of Fatty acid Esters," Prog. Lipid. Res. 1985, v24, pp. 243-267.
Extended Search Report dated Aug. 5, 2011 in corresponding European Patent Application No. 11170379.9.
Du Plessis, J.A.K. et al., "$Re_2O_7/SiO_2.Al_2O_3/SnMe_4$/1-octene catalytic system—Part II. The Incluence of Oxygen Containing Saturated Hydrocarbons on the Metathesis Activity", Journal of Molecular Catalysis A: Chemical, Elsevier, Amsterdam, NL, vol. 133, No. 1-2, Jul. 13, 1998, pp. 181-186.
Schwab P. et al., "Synthesis and Applications of $RUCl_2(=CHR')(PR_3)_2$: The Influence of Alkylidene Moiety on Metathesis Activity", Journal of the American Chemical Society,American Chemical Society, Washington, DC, US, vol. 118, No. 1/05, Jan. 1, 1996, pp. 100-110.

* cited by examiner

*Primary Examiner* — Ling Choi
*Assistant Examiner* — Monique Peets
(74) *Attorney, Agent, or Firm* — Arent Fox, LLP

(57) ABSTRACT

The invention provides a method of preparing a crosslinked polymer, which method comprises polymerising branched polyunsaturated monomers by a metathesis polymerisation reaction, wherein the branched polyunsaturated monomers contain acyclic ethylenically unsaturated groups that are capable of undergoing polymerization by a metathesis reaction such that the metathesis polymerisation produces a crosslinked polymer and substantially no non-volatile ethylenically unsaturated by-products.

9 Claims, No Drawings

CROSSLINKING METHOD

CROSS-REFERENCE TO RELATED APPLICATION

This application is a National Stage entry of International Application No. PCT/AU2006/000930, filed Jun. 30, 2006, the entire specification and claims of which are incorporated herewith by reference.

FIELD OF THE INVENTION

The present invention relates to a method for preparing crosslinked polymers, and to crosslinked polymers prepared by the method. The invention also relates to precursor compositions that can be crosslinked in accordance with the method, and to a method for preparing compounds that can be used to prepare the crosslinked polymers. The method for preparing the crosslinked polymers is particularly suited for use in polymer-based coating and adhesive applications, and accordingly it will be convenient to hereinafter describe the invention with reference to these applications. However, it is to be understood that the method may also be employed in other applications.

BACKGROUND OF THE INVENTION

Crosslinked polymers can generally be characterised as a network of polymer chains in which at least some of the chains are connected through a bridging group. The nature of the bridging can vary significantly, as can the manner in which the bridging group forms its connection with the polymer chains. The number of bridging groups present, that is the degree of crosslinking, in a crosslinked polymer can also vary significantly, with the effective molecular weight, viscosity and solubility of the polymer changing as the degree of crosslinking in the polymer increases. Polymers with any significant degree of crosslinking are generally substantially insoluble in solvents.

Crosslinked polymers typically exhibit superior physical and mechanical properties compared to their non-crosslinked counterparts. The properties of polymer-based coatings and adhesives (i.e. paints, adhesives, fillers, primers and sealants etc) can therefore also generally be improved by providing such products with a crosslinked polymeric structure. However, due to their crosslinked polymer sure, crosslinked polymers are generally not capable of being applied to a substrate in a manner that is required for the application of most coatings and adhesives. In particular, crosslinked polymers cannot generally be moulded into a desired shape or applied as a layer onto the surface of a substrate.

To provide polymer-based coatings and adhesives with a crosslinked structure and an ability to be readily applied to a substrate, the products are often formulated such that crosslinking occurs after the product has been applied to the substrate. One of the more common formulating techniques used to achieve such post-application crosslinking is to provide the product with at least one polymer which contains reactive functional groups. The reactive functional groups afford sites that can react and promote crosslinking post-application of the product.

One approach to providing such products with these reactive functional groups has been to formulate them with unsaturated natural oils (eg. glyceride oils), or alkyd resins formed therefrom. Compositions formulated with these materials make up a large percentage of coatings used globally and axe commonly referred to as air-dry enamels or oil based paints. Drying or curing of such paints essentially results from the reaction of atmospheric oxygen with the ethylenically unsaturated groups derived from the oils, which in turn promotes crosslinking of the composition in a process known as autoxidation.

However, despite being effective at forming crosslinked polymer structures, the autoxidation process is particularly slow. Sufficient crosslinking necessary to apply a second coat of paint without disturbing the first can only be achieved after the film has been allowed to dry over night. Even then, a range of environmental factors such as temperature and humidity can retard the rate of drying.

The process of autoxidation can also continue for a long period of time (i.e. post drying of the paint) and may result in degradation of the physical properties of the paint film. This degradation can limit the performance of such coatings, particularly in an exterior environment. Oil based paints are also prone to yellowing in the absence of direct sunlight. The tendency for these paints to yellow is believed to stem from a variety of atmospheric based reactions of residual unsaturation derived from the fatty acid segments of the polymer.

An alternative approach to providing such products with these reactive functional groups has been to formulate them with a polymer that contains functional groups that will react with water. In this case, the products can be formulated to form a crosslinked structure after application through being exposed to atmospheric moisture. However, due to their inherent moisture sensitivity, great care needs to be taken to exclude moisture during the manufacture, packaging and storage of such products. Despite exercising care to exclude moisture from the products, moisture cure products often have a limited shelf-life.

Coatings and adhesives are also commonly provided in a two-part form where one part includes a polymer which contains functional groups that are reactive toward functional groups of a polymer contained in the other part. In this case, each part is mixed prior to application, and crosslinking occurs post-application through reaction of the respective functional groups provided from each part. The two-part coating and adhesive formulations have the advantage of being generally less sensitive to moisture and therefore often have a good shelf-life. However, by virtue of their reactivity, the individual components cannot be provided in the form of a single-part composition, as would be most convenient. Furthermore, once the two parts are mixed the product must be used within a relatively short time frame.

Although the aforementioned moisture cure and two-part coating and adhesive products effectively form post-application crosslinked polymeric structures, the reactive functional groups used to provide the crosslinking sites can render the products toxic. For example, reactive functional groups commonly used in such products include isocyanates, amines, epoxides and cyano acrylate esters. Accordingly, there can be occupational health and safety risks associated with both the manufacture and use of such products. Furthermore, the monomers comprising the reactive functional groups used in such products are generally relatively expensive.

Another common formulating technique used to achieve post-application crosslinking is to provide products in a two-part form where one part contains a radical initiator and the other part contains a crosslinkable polymer composition. In this case, the initiator is mixed with the polymer composition prior to application, the mixture is then generally immediately applied to a substrate and crosslinking occurs post-application through a radical mediated crosslinking reaction that is promoted by the initiator. As with the previous formulating techniques, this technique also provides for an effective means to achieve post-application crosslinking. However, such polymer compositions are prone to premature and spontaneous crosslinking, the process of which is very exothermic and potentially explosive. These polymer compositions therefore typically need to be formulated with inhibitors to prevent this. Despite the use of inhibitors, the polymer compositions often have a limited shelf-life. Furthermore, initiators commonly used in these products, such as those which contain a peroxy linkage, are typically quite toxic and potentially explosive in their own right.

Accordingly, there remains a need to provide an alternative method for preparing crosslinked polymers that can overcome or alleviate at least some of the disadvantages associated with the aforementioned methods.

SUMMARY OF THE INVENTION

The present invention provides a method of preparing a crosslinked polymer, which method comprises polymerising branched polyunsaturated monomers by a metathesis polymerisation reaction, wherein the branched polyunsaturated monomers contain acyclic ethylenically unsaturated groups that are capable of undergoing polymerisation by a metathesis reaction such that the metathesis polymerisation produces a crosslinked polymer and substantially no non-volatile ethylenically unsaturated by-products.

Typically, the branched polyunsaturated monomers referred to herein will comprise an atom or core to which is attached at least three moieties, at least three of which contain one or more acyclic ethylenically unsaturated groups that are capable of undergoing polymerisation by a metathesis reaction.

It has now been found that branched polyunsaturated monomers can be polymerised by a metathesis pathway to afford a crosslinked polymer structure. The method of the invention is particularly suited for preparing crosslinked polymers that can be used in polymer-based coatings and adhesives, and can be readily employed to provide post-application crosslinking.

As will be discussed in more detail below, the branched polyunsaturated monomers can also be polymerised in conjunction with other unsaturated monomers such as diene monomers.

Those skilled in the art will appreciate that metathesis polymerisation reactions afford a polymer product and an ethylenically unsaturated compound as by-product. In forming crosslinked polymers in accordance with the invention, it is important that the metathesis polymerisation affords substantially no non-volatile ethylenically unsaturated by-products. In other words, in addition to the crosslinked polymer, substantially all by-products of the metathesis polymerisation are volatile ethylenically unsaturated by-products. By being volatile, the ethylenically unsaturated by-products can be more readily separated from the reaction mixture. This not only promotes formation of the crosslinked polymer, but advantageously also allows for the crosslinked reaction product to be effectively used in, for example, paint, adhesive, filler, primer and sealant products etc hereinafter simply referred to as coating(s) and adhesive(s) or coating and adhesive products).

Formation of non-volatile ethylenically unsaturated by-products in the metathesis polymerisation reaction is likely to result in the crosslinked reaction product being unsuitable for use as coating and adhesive products. In particular, the presence of such non-volatile ethylenically unsaturated by-products in coatings and adhesives can prevent them from drying (i.e. they remain tacky), can reduce or inhibit their adhesive or bonding properties, and can in general reduce their physical and/or mechanical properties.

It will be appreciated that whether a given ethylenically unsaturated by-product is non-volatile or volatile will be dependant on both the pressure and temperature at which this property is assessed. In the context of the invention, the terms "non-volatile" and "volatile" are not intended to refer to absolute qualities of a given ethylenically unsaturated by-product, but rather they are to be used as a practical guide in considering the suitability of crosslinked polymer for use as a coating or adhesive. Thus, those metathesis polymerisation reactions that afford substantially no non-volatile ethylenically unsaturated by-products are likely to provide crosslinked polymers that are suitable for use as coatings or adhesives. In this context, "substantially no" will generally mean less that 15 wt %, preferably less than 10 wt %, more preferable less than 5 wt % of non-volatile ethylenically unsaturated by-products, relative to the total mass of ethylenically unsaturated by-products produced by the metathesis polymerisation reaction.

As a convenient point of reference only, in the context of coatings and adhesives, a person skilled in the art might consider the ethylenically unsaturated by-products to be "non-volatile" if they are not vaporised at atmospheric pressure from a coating or adhesive comprising a crosslinked polymer formed in accordance with the invention at (1) room temperature (ca. 15-35° C.) within 24 hours, (2) about 150° C. within about 10 minutes, or (3) about 230° C. within about 30 seconds (i.e. common drying regimes for using such products).

Alternatively, as a convenient point of reference only, in the context of coatings and adhesives a person skilled in the art might consider the ethylenically unsaturated by-products to be "non-volatile" if they contained more than about 12 carbon atoms. In other words, the ethylenically unsaturated by-products preferably contain 2 to about 12, more preferably 2 to about 9 carbon atoms.

Accordingly, the present invention further provides a method of preparing a crosslinked polymer suitable for use as or as part of a coating or adhesive, which method comprises polymerising branched polyunsaturated monomers by a metathesis polymerisation reaction, wherein the branched polyunsaturated monomers contain acyclic ethylenically unsaturated groups that are capable of undergoing polymerisation by a metathesis reaction such that the metathesis polymerisation produces a crosslinked polymer.

A notable advantage provided by the invention is that the crosslinked polymers may be prepared from a diverse array of monomers. In particular, the monomers used need only contain relatively inert acyclic ethylenically unsaturated groups. Thus, such monomers will generally be less toxic than those used to prepare conventional crosslinked polymers, and also generally less prone to premature spontaneous crosslinking. Furthermore, suitable monomers may be provided from relatively inexpensive sustainable resources such as natural oils.

In preparing the crosslinked polymers in accordance with the invention, it may be preferable to use branched polyunsaturated monomers that contain terminal or near terminal acyclic ethylenically unsaturated groups. By using such monomers, formation of non-volatile ethylenically unsaturated by-products can advantageously be reduced if not substantially avoided. By the expression "terminal or near terminal" is meant that the acyclic ethylenically unsaturated groups can be located at the end of an organic moiety (i.e. a vinyl group), or within 6 atoms, preferably within 4 atoms from the end of such a moiety. For example, the unsaturated group(s) may be located within 6 carbon atoms at the end of an organic moiety designated R, i.e. R—C=C—C—C—C—C, R—C—C=C—C—C—C, R—C—C—C=C—C—C, R—C—C—C—C=C—C, or R—C—C—C—C—C=C.

Branched polyunsaturated monomers that contain terminal or near terminal acyclic ethylenically unsaturated groups may be prepared by any suitable means. However, the use of cross-metathesis reactions to prepare these monomers has been found to be particularly convenient.

Accordingly, the invention also provides a method of preparing a crosslinked polymer, which method comprises:
1) preparing branched polyunsaturated monomers having terminal or near terminal acyclic ethylenically unsaturated groups that are capable of undergoing polymerisation by a metathesis reaction, by subjecting a compound comprising one or more acyclic ethylenically unsaturated groups to a cross-metathesis reaction with a low molecular weight ethylenically unsaturated compound to produce a compound comprising one or more terminal or near terminal acyclic ethylenically unsaturated groups which:
   (a) can be used as the branched polyunsaturated monomers, and/or
   (b) is reacted with one or more other compounds to provide a compound which can be used as the branched polyunsaturated monomers; and
2) polymerising the branched polyunsaturated monomers by a metathesis polymerisation reaction to afford the crosslinked polymer.

Through use of such a cross metathesis reaction pathway, branched polyunsaturated monomers derived from inexpensive natural oils can advantageously be used to prepare unique crosslinkable coatings and adhesives. Notably, such methodology enables many so called non-drying or semi-drying natural oils, that have to date been unsuitable for use in coatings and adhesives, to now be used. For example, mono unsaturated triglycerides (i.e. one double bond in each fatty acid arm of the triglyceride) can be readily employed to prepare crosslinkable coatings and adhesives.

The invention therefore also provides a coating (such as a paint) or adhesive product comprising branched polyunsaturated monomers that contain acyclic ethylenically unsaturated groups that are capable of undergoing polymerisation by a metathesis reaction to form a crosslinked polymer, and an olefin metathesis catalyst.

Other aspects of the invention are described below.

DETAILED DESCRIPTION OF THE INVENTION

Unless otherwise stated, where the term "acyclic" is used herein in conjunction with expressions such as "diene monomer", "ethylenically unsaturated group", or "ethylenic unsaturation", or similar expressions, it is intended for this to be a reference to the nature of the unsaturated character of that group or monomer rather than any other facet of that monomer or moiety which contains that group. Thus, a moiety containing an "acyclic" ethylenically unsaturated group may also contain cyclic groups, but the ethylenically unsaturated group per se is acyclic in character in that it is not contained within a cyclic structure. In the case of an "acyclic" diene monomer, only the ethylenically unsaturated groups need be acyclic in character.

The polymerization of acyclic diene monomers by metathesis is generally well known and is commonly referred to as ADMET (acyclic diene metathesis) polymerization. As with all metathesis reactions, ADMET polymerisation involves the reaction of a transition metal alkylidene complex, more commonly referred to as an olefin metathesis catalyst, with an acyclic ethylenically unsaturated group. Mechanistically, propagation of a polymer chain by ADMET polymerisation is believed to involve the formation of two metallocyclobutane intermediate species, with the polymer chain being ejected from the active metal species during each propagation step. The propagation step also involves the liberation of an ethylenically unsaturated reaction by-product, preferably a volatile molecule such as ethylene, which needs to be removed from the reaction environment to promote polymerisation.

ADMET polymerisation reactions inherently afford polymers with a linear unsaturated backbone. Studies have shown that the unsaturated character of these polymers may be used in secondary reactions to provide crosslinking sites. In particular, polymers derived from ADMET polymerisation reactions have been subjected to conventional thermal, ultraviolet and chemical modification processes to afford crosslinked polymer structures (Macromolecules, 1992, 25, 2049-2052).

It has now been found that a metathesis reaction pathway can be used to directly prepare crosslinked polymers in an effective and efficient manner.

In accordance with the invention, crosslinked polymers can be prepared by polymerising branched polyunsaturated monomers. The branched polyunsaturated monomers will typically have at least one atom or core to which is attached at least three moieties, at least three of which contain acyclic ethylenic unsaturation. The atom or core may have more than three moieties attached to it, and more than three moieties may contain acyclic ethylenic unsaturation.

To more clearly describe what is intended by the branched polyunsaturated monomers having "an atom or core to which is attached at least three moieties", the monomers can be conveniently represented as comprising at least the general structural unit (I):

$$BR^1R^2R^3 \tag{I}$$

where B represents an atom or core, and where each moiety $R^1$, $R^2$ and $R^3$, which may be the same or different, contains at least one acyclic ethylenically unsaturated group which is capable of undergoing polymerisation by a metathesis reaction.

The atom or core (B) must be cable of having at least three moieties attached to it, and as such may simplistically be viewed as a branch point or junction. The branched polyunsaturated monomers used in accordance with the invention may have more than one such branch point or junction. In this case, the further branch point(s) or juncture(s) may be provided by other atoms or cores present in one or more of the moieties attached to the atom or core (B) in general structural unit (I). Accordingly, the branched polyunsaturated monomers may comprise both atoms and cores that provide for branch points or junctions.

Where B in the general structural unit (I) is an atom, it will generally be C, Si or N. In the case where the atom is C or Si, the branch atom may have a fourth moiety attached to it which can also contain at least one acyclic ethylenically unsaturated group that is capable of undergoing polymerisation by a metathesis reaction.

By the term "core", as used in connection with the branched polyunsaturated monomers, is meant a molecular structure to which the at least three moieties are attached. For example, the core might be a cyclic aromatic or non-aromatic structure such as that afforded by a benzene or cyclohexane ring, fused derivatives thereof, or possibly a collection of such cycles coupled together by alkyl groups. The core might also be an oligomeric or polymeric structure. In contrast with the general structural unit (I) in which B is an atom, where B is a "core" the number of moieties which contain at least one acyclic ethylenically unsaturated group that can be attached to the core can be considerably higher than four.

As mentioned above, the branched polyunsaturated monomers will typically comprise at least three moieties attached to an atom or core, each of which contain at least one acyclic ethylenically unsaturated group that is capable of undergoing polymerization by a metathesis reaction. By having the ethylenically unsaturated groups configured in this manna, the monomers can advantageously be polymerised by a metathesis reaction to directly afford a crosslinked polymer. In contrast, polymerisation of acyclic diene monomers through a conventional ADMET polymerisation reaction inherently affords polymers having a linear backbone.

Where an acyclic ethylenically unsaturated group is said to be "capable of undergoing polymerisation by a metathesis reaction" or reference is given to a crosslink reaction occurring "through a metathesis mediated reaction pathway", it is intended for these statements to mean that the acyclic ethylenically unsaturated groups of the monomer can react or does react with a metathesis catalyst in the process of forming a crosslinked polymer structure.

Those skilled in the art will appreciate the factors that may effect the susceptibility of a given acyclic ethylenically unsaturated group to undergo polymerisation by a metathesis reaction. For example, moieties which contain the acyclic ethylenically unsaturated groups can impart steric and/or electronic effects that influence the reactivity of the unsaturated groups toward a metathesis catalyst. Furthermore, and as discussed above, to promote the metathesis reaction the ethylenically unsaturated by-product of the reaction, which is itself derived from the monomers being polymerised, should be sufficiently volatile so that it can be removed from the reaction medium.

Generally, the susceptibility of an acyclic ethylenically unsaturated group to undergo polymerisation by a metathesis reaction can be enhanced by reducing steric crowding in the general proximity of the unsaturated group. It may therefore be preferable that the ethylenically unsaturated group contained in each of the at least three moieties attached to the atom or group is a terminal or near terminal acyclic ethylenically unsaturated group, and possibly an unsubstituted terminal or near terminal acyclic ethylenically unsaturated group.

To reduce, if not substantially avoid, the formation of undesirable non-volatile ethylenically unsaturated by-products during the course of the crosslinking reaction, it can be preferable that substantially all of ethylenically unsaturated groups in the monomer are terminal or near terminal acyclic ethylenically unsaturated groups, and possibly unsubstituted (i.e. —CH=CH— or —CH=CH$_2$) terminal or near terminal acyclic ethylenically unsaturated groups.

With an understanding of the function of the acyclic ethylenically unsaturated groups and how they might be configured within the branched monomers, those skilled in the art will also appreciate that apart from the acyclic unsaturated group itself, the structure and composition of the remainder of the monomer is not particularly important with respect to the crosslinking process. Accordingly, any organic group can generally function as a moiety provided it can be attached to an atom or core and contains at least one acyclic ethylenically unsaturated group which is susceptible to undergoing polymerisation by a metathesis reaction. The moieties may therefore comprise cyclic and/or branched and/or linear groups, contain or be substituted with a variety of functional groups, contain one or more hetero atoms such as N, O, S, P etc., and as mentioned above, may even contain one or more further atoms or cores (B) as hereinbefore defined.

One advantage afforded by the invention is that the crosslinked polymers may be prepared using a diverse array of branched polyunsaturated monomers. Having regard to the forgoing, those skilled in the art could readily select suitable monomers. The monomers may have a relatively low molecular weight or can include oligomeric and polymeric compounds. For example, a branched polyunsaturated pre-polymer may be used prepare the crosslinked polymer.

Oligomeric or polymeric branched polyunsaturated monomers that can be used in accordance with the invention may have quite complex structures. For example, the monomers may be in the form of a polymer/oligomer that has a branched or linear backbone onto which is attached at least three moieties as pendant groups, wherein at least three of the pendant groups each contain at least one acyclic ethylenically unsaturated group that is capable of undergoing polymerisation by a metathesis reaction. In practice, such a polymer/oligomer backbone may contain many of these pendant groups, for example greater than 20.

Polymeric/oligomeric branched polyunsaturated monomers may be prepared using conventional polymerisation techniques such as free radical and condensation and metathesis polymerisation techniques.

One such approach might be to prepare the polymeric/oligomeric branched polyunsaturated monomers using monomers that when polymerised afford pendant groups which contain the requisite unsaturated character. In this case, the mode of polymerisation that is used should enable the pendant groups to retain the requisite unsaturated character.

An alternative approach might be to prepare a polymer/oligomer which has reactive functional groups that may be subsequently reacted to provide pendant groups having the requisite unsaturated character. For example, a styrene maleic anhydride copolymer may be prepared by conventional means and subsequently reacted with a reagent such as undecylenic alcohol to afford pendant groups with the requisite unsaturated character.

In both of the approaches mentioned directly above, the number of pendant groups that are attached to the polymer backbone can be advantageously varied through variation of the ratios of monomers used to prepare the polymer/oligomer.

The branched polyunsaturated monomers used in accordance with the invention may also be prepared directly or indirectly through cross-metathesis reactions. For example, to provide branched polyunsaturated monomers which contain terminal or near terminal acyclic ethylenically unsaturated groups, a compound comprising one or more acyclic ethylenically unsaturated groups could be subjected to a cross-metathesis reaction with a low molecular weight ethylenically unsaturated compound. Such compounds would not generally already comprise three or more terminal or near terminal acyclic ethylenically unsaturated groups.

The compound comprising one or more acyclic ethylenically unsaturated groups may be a branched polyunsaturated compound having an atom or core to which is attached at least three moieties, at least three of which contain one or more acyclic ethylenically unsaturated groups, for example a natural oil. In this case, the cross-metathesised product would be a branched polyunsaturated monomer that contains terminal or near terminal acyclic ethylenically unsaturated groups and could be used to prepare a crosslinked polymer in accordance with the invention. The resulting branched polyunsaturated monomer might also be reacted with one or more other compounds or reagents, for example to build the molecular weight of the compound (i.e. to form a pre-polymer). This "modified" branched polyunsaturated monomer might then be used to prepare a crosslinked polymer in accordance with the invention.

A specific example of a cross-metathesis reaction described directly above would be the cross-metathesis reaction of a vegetable oil with ethene as shown below.

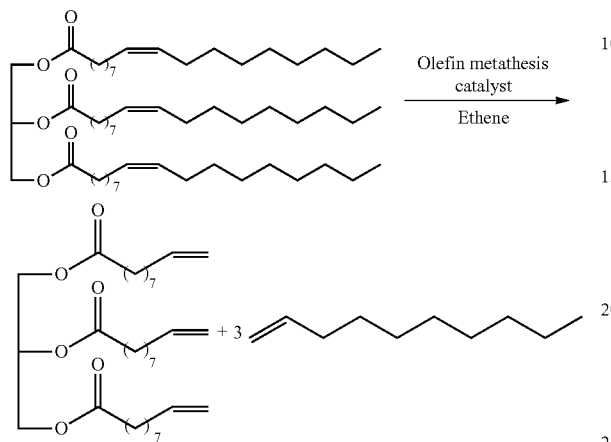

The compound comprising one or more acyclic ethylenically unsaturated groups may also be a branched polyunsaturated compound as described directly above but in the form of a pre-polymer. For example, the compound might be an alkyd resin prepared from the reaction of a monoglyceride with phthalic anhydride. The resin may be subjected to a cross-metathesis reaction with a low molecular weight ethylenically unsaturated compound to afford an alkyd resin comprising terminal or near terminal acyclic ethylenically unsaturated groups that could then be used to prepare a crosslinked polymer in accordance with the invention. An idealized structure of such an alkyd monomer is shown below.

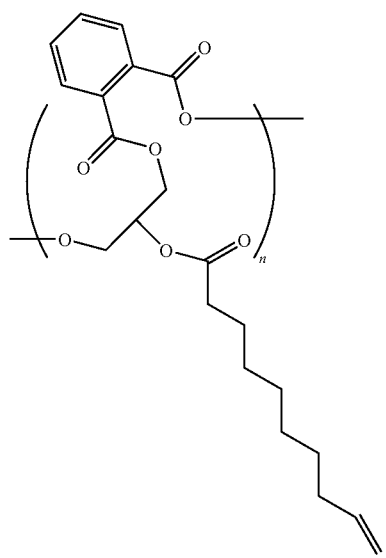

Alternatively, the cross-metathesis reaction might be used to prepare a precursor compound that can be reacted with one or more compounds to form a branched polyunsaturated monomer that may be used to prepare a crosslinked polymer in accordance with the invention. For example, the compound comprising one or more acyclic ethylenically unsaturated groups may be a fatty acid or fatty acid ester derived from natural oils. Such a compound could be subjected to a cross-metathesis reaction with a low molecular weight ethylenically unsaturated compound to afford a terminal or near terminal ethylenically unsaturated fatty acid or fatty acid ester. The resulting compound could then be reacted with one or more compounds to afford the branched polyunsaturated monomers that could be used to prepare a crosslinked polymer in accordance with the invention. In this case, fatty acids or fatty acid esters that would not otherwise be used in coatings and adhesives products can be converted into a valuable resource for such products.

A specific example of a cross-metathesis reaction described directly above would be the cross-metathesis reaction of a fatty acid ester with ethene as shown below.

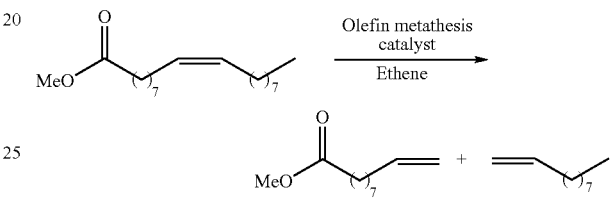

Those skilled in the art will appreciate that the cross-metathesis reactions described above also produce an ethylenically unsaturated reaction by-product. However, unlike the ethylenically unsaturated reaction by-products that can be produced during formation of the crosslinked polymer, the desired terminal or near terminal ethylenically unsaturated compound and the ethylenically unsaturated reaction by-products produced during such cross-metathesis reactions can generally be readily separated from each other.

By "natural oils" is meant oils commonly referred to as vegetable oils, and even fish oil. Such oils must comprise at least one ethylenically unsaturated group, and will generally comprise triglycerides. Examples of suitable natural oils include, but are not limited to, canola oil, soybean oil, flax or linseed oil, tung oil, castor oil, and combinations thereof. Unsaturated fatty acid and fatty acid esters derived from such oils can also be used in accordance with the invention.

By "low molecular weight ethylenically unsaturated compound" in the context of a cross-metathesis reaction is meant a $C_2$-$C_6$ ethylenically unsaturated compound.

Cross-metathesis reactions using low molecular weight simple alkenes have been studied for many years. Of the simple alkenes explored in these cross-metathesis reactions, ethene, as employed in the reactions depicted above, has received the most attention. Cross-metathesis reactions involving ethene are generally referred to as ethenolysis reactions.

Despite considerable research being devoted to studying such ethenolysis reactions, there remain significant problems associated with using this technique to prepare terminal unsaturated compounds, and in particular terminal unsaturated carbonyl compounds. These problems can include poor conversion and selectivity, the need for relatively high catalyst loadings, long reaction times and some limitations on the type of feedstocks.

One significant problem with ethenolysis reactions that has to date proven difficult to overcome is the generation of a methylidene intermediate in the catalytic cycle, Ruthenium methylidene complexes have been shown to have relatively low initiation rates in olefin metathesis reactions. For reactions in which methylidene intermediates are present, sustained metathesis activity can be achieved by increasing temperature. However, this approach also increases the rate of catalyst decomposition resulting in the need for higher catalyst loadings.

A further problem associated with ethenolysis reactions is that the products of the reaction (i.e. terminal olefins) and the ethene can compete with internal olefins present in the starting material in binding to the metathesis catalyst. This results in long reactions times and also has an impact on catalyst loading as significant decomposition of the catalyst can occur during the course of the reaction.

As mentioned, there can be some limitations on the type of feedstocks that may be used in ethenolysis reactions. For example, natural oils that contain conjugated polyunsaturated fatty acids, such as tung oil, are typically poorly converted in ethenolysis reactions. This problem can also extend to other polyunsaturated oils that are not conjugated. For example, ruthenium-based olefin metathesis catalysts have a tendency to catalyse olefin isomerization reactions in addition to olefin metathesis reactions. Thus, 1,4-dienes commonly found in polyunsaturated natural oils can isomerise in the presence of the metathesis catalyst to give conjugated olefins and hence the same problems described above.

Accordingly, there remains a need to provide an alternative method for preparing acyclic unsaturated compounds that can overcome or alleviate at least some of the disadvantages associated with the aforementioned ethanolysis reactions.

The invention further provides a method of preparing near terminal ethylenically unsaturated carbonyl compounds, which method comprises subjecting a carbonyl compound comprising an acyclic ethylenically unsaturated group to a cross-metathesis reaction with substantially pure 2-butene.

It has now been found that substantially pure 2-butene can be used effectively and efficiently in preparing near terminal ethylenically unsaturated carbonyl compounds. The 2-butene may be cis or trans, or a combination thereof, The use of 2-butene in cross metathesis reactions to produce ethylenically unsaturated cabonyl compounds has been reported. However, such reactions have afforded particularly low yields. Without wishing to be limited by theory, it is believed that commercial sources of 2-butene comprise sufficient quantities of impurities that can poison the olefin metathesis catalysts used in such reactions (e.g. ruthenium based metathesis catalysts). Such impurities are believed to at least comprise 1,3-butadiene, a poison for acyclic metathesis reactions. Accordingly, cross metathesis reactions using 2-butene (i.e. butenolysis) to date have been inefficient and practically ineffective.

By using substantially pure 2-butene, cross-metathesis reactions can now advantageously be performed where the productive turn over number (TON) is greater than about 5,000, preferably greater than about 10,000, more preferably greater than about 20,000, most preferably up to 90,000 or higher.

By "substantially pure" 2-butene is meant that the 2-butene is sufficiently free of impurities to enable turn over numbers of greater than about 5,000 to be achieved. Typically, impurities should be present in an amount no greater than about 0.1 mol %, relative to 2-butene.

The use of 2-butene is believed to also advantageously avoid methylidene intermediates being formed during the catalytic cycle, thus circumventing the problems associated with methylidene intermediates in ethenolysis reactions. Another advantage to using 2-butene is that as an internal ethylenically unsaturated compound it competes to a less extent with unreacted ethylenically unsaturated carbonyl compounds to bind to the catalyst compared with ethylene.

The conversion and selectivity of the butenolysis reactions can be controlled by the ratio of 2-butene to the ethylenically unsaturated carbonyl compound. In order to achieve high selectivity and conversion a large excess of 2-butane over the ethylenically unsaturated carbonyl compounds should be used. The reaction can be conducted with or without additional solvent, and preferably either at elevated temperature (>1° C.) and pressure (>1 atm.) or at low temperature ($\leq 1°$ C.) and atmospheric pressure.

Those skilled in the art will appreciate that such butenolysis reactions will afford near terminal ethylenically unsaturated carbonyl compounds in which the ethylenically unsaturated group is located between the second and third atoms of a pendant group. In other words, the ethylenically unsaturated group will be a penultimate terminal ethylenically unsaturated group (i.e. R—C—C—C—C=C—C).

The butenolysis reaction in accordance with the invention may conveniently be preformed using a diverse array of ethylenically unsaturated carbonyl compounds. By "ethylenically unsaturated carbonyl compound" is meant an ethylenically unsaturated compound that comprises one or more carbonyl functional groups such as an ester, an amide, a ketone, an aldehyde or a carboxylic acid. Having regard to the forgoing, those skilled in the art could readily select suitable ethylenically unsaturated carbonyl compounds for this purpose.

The butenolysis reaction in accordance with the invention may conveniently be preformed using unsaturated natural oils, or fatty acids or fatty acid esters derived therefrom, to prepare near terminal ethylenically unsaturated carbonyl compounds. The butenolysis reaction is particularly suited for use in preparing branched polyunsaturated monomers that may be crosslinked in accordance with the invention. For example, the butenolysis reaction may be used to prepare branched polyunsaturated monomers from linseed oil as illustrated below.

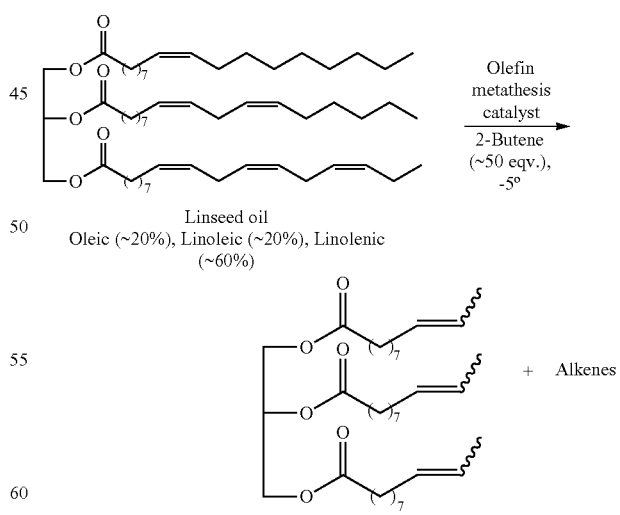

The method of preparing a crosslinked polymer in accordance with invention can advantageously be performed in numerous ways and under a variety of conditions. Such versatility stems in part from the ability to provide the branched polyunsaturated monomers in either a liquid or a solid form, and also the ability to select the monomers such that they can be polymerised by the metathesis reaction at ambient temperatures.

To accelerate the rate of crosslinking and produce tightly crosslinked and inert coatings, industrial processes, such as the coating of automotive bodies or continuous coil with crosslinkable coatings, are often performed at elevated temperature (i.e. up to about 240° C.). However, for temperature sensitive substrates or consumer applications where the use of high temperature is not convenient or not possible, it is highly desirable to employ crosslinking reactions that are accessible at room temperature or only with moderate degree heating (i.e. temperatures less than 100° C.). Such crosslinking reactions will of course still be accelerated if more heat is applied, but the main advantage is that the reactions are available for consumer application. The crosslinking method in accordance with the invention is particularly well suited for such consumer applications.

In performing the method of the invention, the necessary reagents may be provided in a variety of different two-part systems. The coatings and adhesives products of the invention may be conveniently provided in the form of such two-part curable systems.

A simple two-part system may comprise a first part which comprises branched polyunsaturated monomers suitable for reaction in accordance with the present invention, and a second part which comprises a metathesis catalyst. The formulations of each part can readily be mixed prior to application to enable crosslinking to occur post-application through a metathesis mediated reaction pathway.

One advantage such two-part systems may provide over conventional two part systems is that once the two parts are mixed, the crosslinking reaction can be retarded simply by enclosing the mixture in a sealed container. By confining the mixture in this way, volatile alkene by-products are restricted from leaving the reaction environment and the metathesis reaction can be retarded. This in turn can extend the products workable application time post mixing.

Depending upon the nature of the monomer and catalyst, crosslinking may occur at ambient temperatures, or it may be necessary to apply heat to the mixed two-part formulation to promote crosslinking. An example of where it may be necessary to apply heat to promote crosslinking is where the monomer is provided in solid form. In solid form, the monomer can be conveniently powdered and applied to a substrate using conventional powder coating technology. The catalyst can then be applied to the monomer by a technique such as spraying. Alternatively, due to there being limited reactivity between the catalyst and the solid monomer, the catalyst may be combined with the powdered monomer before it is applied to the substrate. In order to promote crosslinking, the catalyst/monomer combination can be heated by well known methods such as inferred (IR) irradiation. Under these circumstances, sufficient heat is generally applied to cause the monomer to melt.

As an alternative two-part system, the first part may comprise branched polyunsaturated monomers and acyclic diene monomers, and the second part may comprise the metathesis catalyst. This two-part system may be utilised in much the same way as the system discussed above. However, in this case the presence of the acyclic diene monomers provides considerable flexibility in being able to adjust the composition and architecture of the resulting crosslinked polymer. Notably, the crosslink density of the resulting crosslinked polymer can be readily adjusted. For example, by providing the first part with diene monomers the crosslink density of the resulting crosslinked polymer can be reduced. Conversely, by providing the first part with little or no diene monomers the crosslink density of the resulting crosslinked polymer can be increased.

Accordingly, the method of the invention may further comprise polymerising acyclic diene monomers by the metathesis polymerisation reaction.

It should also be noted that the crosslink density of the crosslinked polymers prepared in accordance with the invention can also be varied by changing the nature of the branched polyunsaturated monomers. In this case, by having the acyclic ethylenically unsaturated groups of the monomer in closer proximity to each other the crosslink density of the resulting crosslinked polymer will generally be higher than if the unsaturated groups were more spaced apart.

Thus, through variation of tee nature of the branched polyunsaturated monomer and the use of acyclic diene monomers, the method provides for considerable flexibility in being able to adjust the composition and architecture of the resulting crosslinked polymer.

When used in conjunction with the branched polyunsaturated monomers in preparing the crosslinked polymers, the acyclic diene monomers should also react with the metathesis catalyst during the crosslinking process. Accordingly, the diene monomers must have at least two ethylenically unsaturated groups that are susceptible to undergoing polymerisation by a metathesis reaction. Suitable acyclic diene monomers are generally well known and readily available. In particular, those monomers suitable for use in a conventional ADMET polymerisation may be used as acyclic diene monomers.

Acyclic diene monomers used in conjunction with the branched polyunsaturated monomers can be in either liquid or solid form. Where both the branched acyclic polyunsaturated monomer and the diene monomer are in solid form, both monomers can conveniently be melt mixed, for example by extrusion, and subsequently powdered for use in a powder coating process as described above.

An alternative two-part system may also comprise a first part which comprises branched polyunsaturated monomers suitable for reaction in accordance with the present invention, and a second part which comprises a polymer prepared by ADMET polymerisation. In this case, it is important that the ADMET derived polymer retains an active catalyst component. By "retains an active catalyst component" is meant that the polymer reaction product of the ADMET polymerisation reaction has associated with it metathesis catalyst which is capable of promoting further polymerisation reactions.

In this particular two-part system, the formulations of each part may be mixed prior to application to enable to crosslinking occur post-application through a metathesis mediated reaction pathway. However, unlike the previous two-part systems, the catalyst component is provided by an ADMET derived polymer. In this case, the catalyst in effect remains dormant until the components of each part are combined. This two-part system may be utilised in much the same way as the systems described above. For example, the monomers and ADMET derived polymer may be provided in solid form and applied by powder coating techniques. Alternatively, the monomers and/or ADMET derived polymer may be solvated with a suitable solvent to provide for a liquid curable system.

The method of preparing a crosslinked polymer in accordance with the invention may be performed as a bulk polymerisation or in an organic solvent. By providing the branched polyunsaturated monomers as low viscous liquids, or in solid form, the two-part systems described above may be formulated using little if no organic solvent. The ability to use little if no organic solvent in such systems is a particularly advantageous given the onerous legislative requirements regarding the permissible volatile organic content (VOC) of coating and adhesive products that apply in many countries.

The method of crosslinking polymers in accordance with the invention can be readily applied to provide effective coatings and adhesives. The coating and adhesives in accordance with the invention comprise branched polyunsaturated monomers that contain acyclic ethylenically unsaturated groups that are capable of undergoing polymerisation by a metathesis reaction to form a crosslinked polymer, and an olefin metathesis catalyst. Those skilled in the art will have an understanding of other suitable formulation components that may also be included in the coating and adhesives. Examples of such formulation components include, but are not limited to, thickeners, antifungal agents, UV absorbers, extenders, pigments and tinting agents.

The cured product formed from the coatings and adhesives in accordance with the invention may comprise polymer material not formed through the metathesis crosslinking reaction. Accordingly, the coatings and adhesives may be formulated as a blend with other polymers and/or monomers that are not formed from or take part in the metathesis polymerisation reaction.

A notable advantage of the coatings and adhesives in accordance with the invention is that the products crosslinked polymer structure is not formed via autoxidation. As previously mentioned, the process of autoxidation can continue for a long period of time (i.e. post drying of the coating or adhesive) and may result in degradation of the physical properties of the coating or adhesive. For example, in oil based paints degradation of the crosslinked polymer can lead to pigment particles at the surface of the paint film becoming exposed and result in a problem known as chalking. Oil based paints are also prone to yellowing due to the presence or formation of residual conjugated unsaturation in the polymer that forms the paint film.

Unlike the progressive nature of autoxidation, the metathesis mediated reaction pathway that operates in the crosslinking method of the invention occurs within a finite time frame uniformly throughout the composition. Furthermore, feedstock monomers for the metathesis crosslinking reactions are unlikely to contain or give rise to a residual conjugated unsaturation in the resulting crosslinked polymer product. Thus, the crosslinked polymer products in accordance with the invention will typically maintain their physical properties and be less prone to yellowing over time compared with products formed by conventional means.

The present invention involves the use of an olefin metathesis catalyst. Those skilled in the art could readily select and obtain suitable catalysts to perform the invention. Examples of suitable olefin metathesis catalyst include, but are not limited to, Grubbs Catalyst 1st generation, or Benzylidene-bis(tricyclohexylphosphine)dichlororuthenium, Grubbs Catalyst 2nd Generation, or Benzylidene[1,3-bis(2,4,6-trimethylphenyl)-2-imidazolidinylidene]dichloro(tricyclohexylphosphine)ruthenium, and Hoveyda-Grubbs Catalyst 2nd Generation, or 1,3-Bis-(2,4,6-trimethylphenyl)-2-imidazolidinylidene) dichloro(o-isopropoxyphenylmethylene)ruthenium.

For butenolysis reactions and cross-linking with butenolysis products, Grubbs Catalyst 2nd Generation and Hoveyda-Grubbs Catalyst 2nd Generation are preferred.

The olefin metathesis catalyst may be provided in any suitable form that enables it to promote polymerisation. For example, the catalyst may be combined with a suitable carrier material such as a solvent or perhaps a solid and formed into a tablet. It will be appreciated that any such carrier material should be compatible with other components of the curable systems.

EXAMPLES

Example 1

Butenolysis of Triolein

A schlenk tube equipped with a magnetic stirrer bar was evacuated then filled with argon and placed in a methanol bath which was cooled to −5° C. The tube was charged with cis-2-butene (1.30 g, 23.2 mmol) and triolein (0.75 mL, 7.7 mmol). A solution of Hoveyda-Grubbs Second Generation Catalyst (0.145 μg, 2.32 nmol) in dichloromethane (10 μl) was added to the tube and the mixture was stirred using a magnetic stirrer for 256 minutes. After this time the reaction was quenched by addition of ethyl vinyl ether (500 μL). A sample of the product was trans-esterified with methanol by conventional means and analysis of the trans-esterification product by Gas Chromatography (GC) showed a conversion of >90% the oleic chains to 9-undecenoic chains. This conversion equates to a TON of >90,000 for the catalyst.

Example 2

Butenolysis of Methyl Oleate with 2-butane of Varying Purity

Schlenk tubes equipped with a magnetic stirrer bar was evacuated then filled with argon and placed in a methanol bath which was cooled to −5° C. Various samples were prepared using samples of 2-butene from various sources;
Sample A (comparative): cis+trans 2-butene (contains 2.6% of 1,3 butadiene)
Sample B: cis-2-butene (free of 1,3 butadiene)
Sample C (comparative): c is 2-butene (free of 1,3 butadiene) doped with 2% butadiene The quantity of 2-butene added in each case was the same (1.30 g, 23.2 mmol). A quantity of singly distilled methyl oleate (1.45 mg, 488 mmol) and a solution of Hoveyda-Grubbs Second Generation Catalyst (0.145 μg, 2.32 nmol) in dichloromethane (10 μL) was added to the tube and the mixture was stirred using a magnetic stirrer for 256 minutes. After this time the reaction was quenched by addition of ethyl vinyl ether (500 μL). The samples were analysed by GC and the degree of conversion of the oleic chains to 9-undecenoic chains compared.
Results:

| Sample A | trace << 1% conversion |
| Sample B | >90% conversion |
| Sample C | trace << 1% conversion |

Example 3

Butenolysis of Methyl Oleate

A stainless steel autoclave with a glass liner was equipped with a magnetic stirrer bar and charged with ethyl oleate (0.34 g, 1.1 mmol) and Second Generation Grubbs Catalyst (9.3 mg, 0.11 μmol). The autoclave flushed with argon. The autoclave was evacuated and then pressurised with cis-2-butene to a pressure of 15 psi. The autoclave was heated at 60° C. with stirring overnight. The pressure was then released and ethyl vinyl ether (50 μL) added to the reaction mixture. A sample of the product was trans-esterified with methanol by conven-

Example 4

Butenolysis of Canola Oil

A 2 L round bottomed flask equipped with a magnetic stirrer bar was immersed in a methanol bath. The flask was charged with canola oil (80.97 g), then evacuated and the oil stirred rapidly for 1 hour. The flask was then filled with argon and the methanol bath was cooled to −7° C. The flask was then charged with cis+trans-2-butene (204.5 g, 3.65 mol).

A solution Hoveyda-Grubbs Second Generation Catalyst (11.4 mg, 0.18 µmol) in dichloromethane (1 mL) was added to the flask and the mixture was stirred using a magnetic stirrer for 64 minutes. After this time tricyclohexylphosphine (0.15 g) was added to the mixture. The temperature of the bath was raised slowly to ~40° C. and the volatiles collected by distillation. A small sample of the product was trans-esterified with methanol by conventional means and analysis of the trans-esterification product by GC showed a conversion of >95% the unsaturated fatty acid chains to 9-undecenoic chains.

Example 5

Butenolysis of a Soya-based Alkyd Resin

A 2 L round bottomed flask equipped with a magnetic stirrer bar was immersed in a methanol bath cooled to −10° C. The flask was evacuated and filled with argon. The flask was charged with a de-gassed solution of a soya-based alkyd resin (90 g) in dichloromethane (100 mL), cis+trans-2-butene (166 g, 2.96 mol) and Hoveyda-Grubbs Second Generation Catalyst (0.10 g, 16.0 mmol). The mixture was stirred using a magnetic stirrer for ~90 minutes. After this time additional Hoveyda-Grubbs Second Generation Catalyst (0.10 g, 16.0 mmol) was added to the reaction and stirring was continued for a further 60 minutes. Tricyclohexylphosphine (0.10 g) was added to the mixture. The temperature of the bath was raised slowly to room temperature and the volatiles were collected by distillation. Air was bubbled through the remaining solution overnight. A small sample of the product was trans-esterified with methanol by conventional means and analysis of the trans-esterification product by GC showed a conversion of >90% the unsaturated fatty acid chains to undec-9-enoic chains. Additional volatile compounds were removed from the product by heating the product at 150° C. in a high vacuum for 15 minutes.

Example 6

Preparation of 2,2-bis((undec-10-enoyloxy)methyl)propane-1,3-diyl diundec-10-enoate Trimethylolpropane (2.73 g, 20.34 mmol), undecenylenic acid (15.0 g, 81.39 mmol, 4 equiv.) and DMAP (0.99 g, 8.136 mmol, 0.4 equiv.) were dissolved in tetrahydrofuran (150 ml) and the mixture was cooled to 0° C. DCC (16.77 g, 81.39 mmol, 4 equiv.) in tetrahydrofuran (45 ml) was added dropwise to the mixture and kept at 0° C. for 30 mins then allowed to warm to 20° C. and stirred for 3 days. The mixture was filtered (to remove N,N-dicyclohexyl urea) to remove precipitate. The remaining clear liquid was reduced under partial pressure. The residue was taken up in ether, washed with sodium carbonate (10% aqueous solution), brine, dried over magnesium sulfate, filtered and reduced under partial pressure. The crude material was purified by flash chromatography (ethyl acetate/hexane 5/95) to give 9.55 g (74%) of ethane-1,1,1-triyl triundec-10-enoate as a yellow oil; IR (film) 3467, 3076, 2922, 2855, 2120, 1746, 1640, 1464, 1417, 1386, 1355, 1236, 1158, 1116, 1056, 994, 909, 783, 724 cm$^{-1}$; $^1$H NMR (CDCl$_3$): δ=5.90-5.72 (m, 3H), 5.04-4.87 (m, 6H), 4.00 (s, 6H), 2.28 (t, 6H, J=2.26 Hz), 2.07-1.99 (m, 6H), 1.62-1.55 (m, 6H), 1.52-1.43 (m, 2H), 1.42-1.34 (m, 30H), 0.88 (t, 3H, J=2.12 Hz); $^{13}$C NMR (CDCl$_3$): δ=173.2, 138.9, 114.0, 63.6, 40.5, 34.1, 33.6, 29.2, 29.1, 29.0, 28.9, 28.7, 24.8, 23.0, 7.2; MS-ESI m/z 655.6 (M+Na$^+$). Anal. Calcd for C$_{39}$H$_{68}$O$_6$; C, 74.00; H, 10.83. Found: C, 73.98; H, 11.01.

Example 7

Preparation of 2-ethyl-2-((undec-10-enoyloxy)methyl)propane-1,3-diyl diundec-10-enoate Pentaerythrilol (2.94 g, 21.59 mmol), undecenoic acid (20.0 g, 108.53 mmol, 5 equiv.) and DMAP (1.32 g, 10.85 mmol, 0.5 equiv.) were dissolved in THF (150 ml) and the mixture was cooled to 0° C. DCC (22.28 g, 108.53 mmol, 5 equiv.) in THF (50 ml) was added dropwise to the mixture and kept at 0° C. for 30 minutes then allowed to warm to 20° C. and stirred for 3 days. The mixture was filtered then reduced under partial pressure. The residue was taken up in ether (200 ml) and washed with Na$_2$CO$_3$ (10% aqueous solution), brine, dried over MgSO$_4$, filtered and reduced under partial pressure. The crude material was purified by flash chromatography (EtOAc/Hexane 5/95) to give 12.65 g (72%) of 2-ethyl-2-((undec-10-enoyloxy)methyl)propane-1,3-diyl as a yellow oil; IR (film) 3469, 3076, 2926, 2855, 1745, 1640, 1466, 1416, 1389, 1355, 1235, 1157, 1116, 994, 909, 724 cm$^{-1}$; $^1$H NMR (CDCl$_3$): δ=5.86-5.72 (m, 4H), 5.01-4.89 (m, 8H), 4.10 (s, 8H, CCH$_2$O), 2.31-2.26 (m, 8H), 2.06-1.99 (m, 8H), 1.63-1.53 (m, 8H), 1.42-1.22 (m, 40H); $^{13}$C NMR (CDCl$_3$); δ=173.1, 139.0, 114.1, 62.1, 41.83, 34.0, 33.7, 29.2, 29.1, 29.0, 28.9, 28.8, 24.8; MS-ESI m/z 801.8 (M+H)$^+$. Anal. Calcd. for C$_{49}$H$_{84}$O$_8$: C, 73.46; H, 10.57. Found: C, 73.39; H, 10.65.

Example 8

Preparation of the Diester of Biphenol A and 10-undecenoic Acid 2,2-diallybisphenol A (1.577 g, 5.11 mmol) and undecenoic acid chloride (3.11 g, 15.34 mmol, 3 equiv.) were combined together and the mixture was heated at 60° C. for 16 hours. The mixture was taken up in ether (50 ml) and washed with sodium hydrogen carbonate (saturated aqueous solution) (3×50 ml) then washed with brine (2×40 ml), dried over anhydrous magnesium sulfate, filtered and reduced under partial pressure. The crude material was purified by flash chromatography (ethyl acetate/hexane 5/95) to give 3.11 g (95%) of the product as a pale yellow oil; $^1$H NMR (CDCl$_3$): δ=7.09-7.04 (m, 4H), 6.92-6.90 (m, 2H), 5.90-5.77 (m, 4H), 5.04-4.92 (m, 8H), 6.50 (d, 4H, J=6.3 Hz), 2.54 (t, 4H, J=7.5 Hz), 2.08-2.01 (m, 4H), 1.77-1.70 (m), 1.64 (s, 6H), 1.43-1.32 (bs, 24H); $^{13}$C NMR (CDCl$_3$): δ=172.8, 148.3, 147.1, 139.4, 136.3, 131.2, 128.9, 126.2, 121.9, 116.7, 114.4, 42.7, 35.1, 34.6, 34.0, 31.2, 29.5, 29.4, 29.3, 29.2, 29.1, 25.2; MS-ESI m/z (M+H)$^+$. Anal. Calcd. for C$_{43}$H$_{60}$O$_4$: C, 80.58; H, 9.44. Found: C, 78.81; H, 9.30.

Example 9

Cross-Linking of the Butenolysis Product of Canola Oil to Give a Film

Simple alkenes were removed from the butenolysis product of canola oil (e.g. the product derived from Stage 1 of Example 4) by vacuum distillation leaving a pale yellow oil. A sample of this oil (0.46 g) was mixed with titanium dioxide (0.29 g) and ground to a homogeneous mixture. This mixture was placed on a microscope slide and a solution of Hoveyda-Grubbs Second Generation Catalyst (15 mg) in dichloromethane (10 μL) added and mixed thoroughly. The mixture was spread to cover an area of 40×60 mm. After 1 hour the film was found to have set to a solid film and have lost 0.025 g in mass. The film was found to be insoluble in the following solvents: water; methanol; acetone; ethyl acetate; hexane; toluene.

Example 10

Cross-Linking of an Alkyd Resin Based on 9-undecenoic Acid to Give a Film

A sample of the product of Example 5 (1.0 g) was ground to a homogeneous mixture with titanium dioxide (0.63 g) and toluene 0.5 mL. Hoveyda-Grubbs Second Generation Catalyst (15 mg) was mixed thoroughly into the mixture, which was then painted onto a microscope slide. After 10 minutes the film had set to give a glossy surface. This film which was initially slightly soft, became progressively harder over the next 12 hours to finally give a hard tough film which adhered well to the glass. The film was found to be insoluble in the following solvents: water; methanol; acetone; ethyl acetate; hexane; toluene.

Colour Comparison

A film derived from the experimental white pigmented paint was compared to a film derived from a commercially available white pigmented alkyd paint (Dulux High Gloss Enamel). Films of the experimental sample and commercial product were cast onto a sealed panel using a #40 wire drawdown bar and the films dried fully over 48 hours. The colour difference between experimental and commercial films was compared to the same reference white tile and the colour difference coordinates calculated using a CIE1976 colour system. Aging of the samples was then accelerated by taking the same panel and taping it to the inside of a metal can having a close fitting lid into which 5 ml of a 10% solution of ammonium hydroxide was placed to saturate the atmosphere in the can. The panel was exposed to these conditions for 48 hours.

Results:

|  |  | Delta L | Delta a | Delta b |
|---|---|---|---|---|
| Example 10 | Before ammonia exposure | −0.70 | 0.03 | 0.47 |
|  | After ammonia exposure | −0.35 | −0.25 | 1.33 |
| Commercial sample (comparative) | Before ammonia exposure | 0.10 | −0.69 | 1.77 |
|  | After ammonia exposure | −2.69 | −0.42 | 12.74 |

The substantial difference in yellowness (+1.30) between the experimental sample and the comparative sample prior to being exposed to ammonia was clearly evident by eye. The effect of ammonia exposure is a test well known as correlating with the tendency of conventional enamels to yellow over time. After ammonia exposure, the comparative sample showed significantly more yellowing (+11.41). Due to the absence of autoxidation in the film derived from the experimental sample, these results are expected to reflect the difference that would be attained through natural exposure over time. In other words, the crosslinked film in accordance with the invention is expected to undergo little if no yellowing over time.

Example 11

Cross-Linking of 2-ethyl-2-((undec-10-enoyloxy)methyl)propane-1,3-diyl diundec-10-enoate to Give a Film First Generation Grubbs Catalyst (10 mg) was dissolved in a minimum volume of dichloromethane and mixed with 2-ethyl-2-((undec-10-enoyloxy)methyl)propane-1,3-diyl diundec-10-enoate (0.80 g). The mixture was spread onto a petridish. After 17 hours the mixture had become a hard and rubbery film.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method of preparing a crosslinked polymer, wherein the method comprises polymerising branched polyunsaturated monomers by a metathesis polymerisation reaction, wherein the branched polyunsaturated monomers comprise at least a general structural unit (I):

$BR^1R^2R^3$         (I)

where B represents an atom or core, and where each moiety $R^1$, $R^2$ and $R^3$, which may be the same or different, contains at least one acyclic ethylenically unsaturated group which (a) is located within 6 atoms from the end of the moiety, and (b) is capable of undergoing polymerization by a metathesis reaction such that the metathesis polymerisation produces a crosslinked polymer and substantially no non-volatile ethylenically unsaturated by-products, wherein the branched polyunsaturated monomers are, or are derived from, a natural oil.

2. The method according to claim 1 which further comprises polymerising acyclic diene monomers by the metathesis polymerisation reaction.

3. The method according to claim 1, wherein the acyclic ethylenically unsaturated groups are unsubstituted.

4. The method according to claim 1, wherein the natural oil is selected from the group consisting of canola oil, soybean oil, flax oil, linseed oil, tung oil, castor oil, and combinations thereof.

5. The method according to claim 1, wherein the branched polyunsaturated monomers are prepared directly or indirectly from a cross-metathesis reaction.

6. The method according to claim 1, wherein the branched polyunsaturated monomers are prepared by subjecting a compound that:
   (a) is, or is derived from, a natural oil, and
   (b) comprises one or more acyclic ethylenically unsaturated groups;

to a cross-metathesis reaction with a low molecular weight ethylenically unsaturated compound to produce a compound which:
(i) comprises at least the structural unit (I) and is used as the branched polyunsaturated monomers, and/or
(ii) is reacted with one or more compounds to produce a compound which comprises at least the structural unit (I) and is used as the branched polyunsaturated monomers.

7. The method according to claim 6, wherein the compound comprising one or more acyclic ethylenically unsaturated groups used to prepare the branched polyunsaturated monomers is a fatty acid derived from a natural oil, or fatty acid ester derived from a natural oil.

8. The method according to claim 6, wherein the low molecular weight ethylenically unsaturated compound is substantially pure 2-butene.

9. The method according to claim 6, wherein the natural oil is selected from the group consisting of canola oil, soybean oil, flax oil, linseed oil, tung oil, castor oil, and combinations thereof.

* * * * *